US009505507B2

(12) United States Patent
Yamagata et al.

(10) Patent No.: US 9,505,507 B2
(45) Date of Patent: Nov. 29, 2016

(54) CAP OPENING AND CLOSING MECHANISM AND AUTOMATIC ANALYZER INCLUDING THE SAME

(75) Inventors: Toshiki Yamagata, Tokyo (JP); Kenichi Takahashi, Tokyo (JP); Takahiro Sasaki, Tokyo (JP); Shigeki Yamaguchi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 135 days.

(21) Appl. No.: 14/129,667

(22) PCT Filed: Jun. 26, 2012

(86) PCT No.: PCT/JP2012/066271
§ 371 (c)(1),
(2), (4) Date: Jan. 31, 2014

(87) PCT Pub. No.: WO2013/002216
PCT Pub. Date: Jan. 3, 2013

(65) Prior Publication Data
US 2014/0174028 A1 Jun. 26, 2014

(30) Foreign Application Priority Data
Jun. 30, 2011 (JP) ................... 2011-145166

(51) Int. Cl.
*B65B 7/28* (2006.01)
*G01N 35/00* (2006.01)
*B01L 3/00* (2006.01)

(52) U.S. Cl.
CPC ............... *B65B 7/28* (2013.01); *G01N 35/00* (2013.01); *B01L 3/50825* (2013.01); *G01N 2035/00287* (2013.01)

(58) Field of Classification Search
CPC .................. B65B 7/28; G01N 35/00
See application file for complete search history.

(56) References Cited

U.S. PATENT DOCUMENTS

2003/0061911 A1* 4/2003 Niwayama et al. ............. 81/3.2
2005/0210671 A1* 9/2005 Itoh ........................... B67B 7/02
29/801

(Continued)

FOREIGN PATENT DOCUMENTS

EP 2282212 A1 2/2011
JP 5-264418 A 10/1993

(Continued)

OTHER PUBLICATIONS

Machine English Translation JP5264418A, No Date.*

(Continued)

*Primary Examiner* — Jill Warden
*Assistant Examiner* — Julie Tavares
(74) *Attorney, Agent, or Firm* — Mattingly & Malur, PC

(57) ABSTRACT

An automatic analyzer of the present invention includes: a cap opening and closing mechanism including a plurality of types of support bodies, each being adaptable to a specific type of cap; an information control mechanism for sample containers; a cap opening and closing mechanism that performs uncapping and capping operations based on a sample container identifying process; and an uncapping/capping monitoring mechanism that determines an uncapping or capping operation. The cap opening and closing mechanism is thus configured so as to be capable of performing the uncapping and capping processes for different types of caps. This provides a cap opening and closing mechanism that enables the single cap opening and closing mechanism to perform the uncapping process and the capping process for different types of caps on a transfer path of sample containers in the automatic analyzer.

15 Claims, 19 Drawing Sheets

(56) References Cited

U.S. PATENT DOCUMENTS

| | | | |
|---|---|---|---|
| 2008/0170967 A1* | 7/2008 | Itoh | B67B 7/02 422/400 |
| 2011/0088517 A1 | 4/2011 | Tsujimura et al. | |

FOREIGN PATENT DOCUMENTS

| | | |
|---|---|---|
| JP | 9-243643 A | 9/1997 |
| JP | 11-304809 A | 11/1999 |
| JP | 2003-14770 A | 1/2003 |
| JP | 4210306 B2 | 10/2008 |
| JP | 2009-36511 A | 2/2009 |
| JP | 2009-264878 A | 11/2009 |
| JP | 2012-159317 A | 8/2012 |
| WO | 2009/141957 A1 | 11/2009 |
| WO | 2013/002213 A1 | 1/2013 |

OTHER PUBLICATIONS

International Preliminary Report on Patentability received in International Application No. PCT/JP2012/066271 dated Jan. 16, 2014.
Extended European Search Report received in corresponding European Application No. 12804159.7 dated Mar. 17, 2015.

* cited by examiner

Fig.2B1
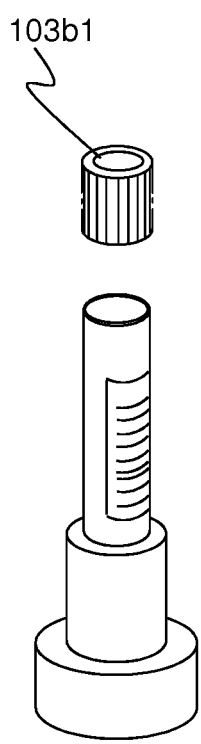

Fig.2B2
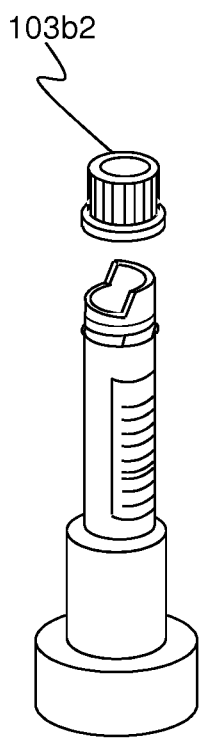

Fig.4B1
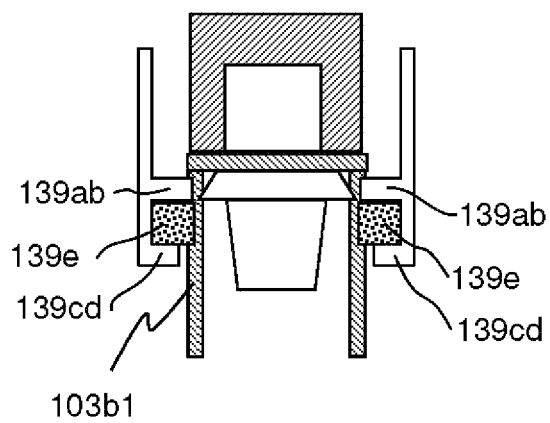

Fig.4B2
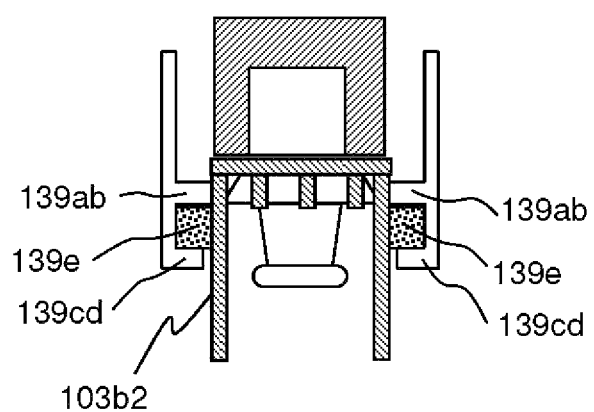

CAP OPENING AND CLOSING MECHANISM AND AUTOMATIC ANALYZER INCLUDING THE SAME

TECHNICAL FIELD

The present invention relates to a cap opening and closing mechanism that automatically opens or closes a cap that can be mounted on a container storing therein a liquid sample, such as blood and urine. The present invention also relates to an automatic analyzer that includes the cap opening and closing mechanism and performs a process on a container that has undergone a cap opening process.

BACKGROUND ART

An automatic analyzer includes an analyzer that measures a physical property of a sample (e.g., a biological sample, such as serum and blood, or a mixture of a biological sample with a reagent), a sample processor that processes a sample in advance of measurement of a physical property of the sample, or a system that integrates the analyzer with the sample processor. The automatic analyzer includes processing units that perform a container cap opening process, a pipetting process, a container cap closing process, a mixing process, an analyzing process, and others and a transfer mechanism that transfers samples among different processing units.

The container cap opening process performs an uncapping process relative to a sample container on which a cap is mounted, wherein the cap on the sample container is opened. The pipetting process takes part out of the sample stored in the sample container after having been opened and discharges the part to another container. The container cap closing process performs a capping process relative to the sample container that has undergone predetermined processes including the pipetting process, wherein the cap on the sample container is closed again. The mixing process mixes the pipetted sample to thereby make its contents uniform. The analyzing process takes qualitative and quantitative measurements of the contents of the pipetted sample in which reaction is underway or completed.

Known arrangements for opening and closing the cap of the sample container (hereinafter referred to as an uncapping process and a capping process) in the container cap opening process and the container cap closing process of the sample processor are disclosed, for example, in Patent Documents 1 to 3.

PRIOR ART DOCUMENTS

Patent Documents

Patent Document 1: JP-4210306-B
Patent Document 2: JP-2009-36511-A
Patent Document 3: JP-11-304809-A

SUMMARY OF THE INVENTION

Problem to be Solved by the Invention

The cap opening means disclosed in Patent Document 1 is intended for automatically uncapping a capped test tube. The uncapping method disclosed in Patent Document 1 is, however, applicable only to a type of sample container in which a cap formed of rubber or synthetic resin is press-fitted in place. Thus, the method is not capable of uncapping a screw-capped sample container.

The cap opening device disclosed in Patent Document 2 is concerned with a mechanism for uncapping sample containers capped with caps of varying lengths, diameters, and shapes. Patent Document 2 does not, however, mention any capping process that reuses an uncapped cap. The method disclosed in Patent Document 2 may therefore cause an uncapped cap that has undergone the uncapping process to be damaged or deformed, so that the uncapped cap may not be good for reuse.

Patent Document 3 discloses a cap for capping various types of blood collection tubes having different lengths and thicknesses and an uncapping mechanism therefor. The method disclosed in Patent Document 3 allows a single type of cap compatible with many different types of blood collection tubes to be applied to capping different types of blood collection tubes. This method, however, requires that a cap dedicated to capping be used for capping different types of sample containers. This may involve cost for the uncapping and capping processes and a large number of caps contaminated with samples being discarded.

In view of the foregoing situation, an object of the present invention is to provide an automatic analyzer including a cap opening and closing mechanism capable of performing an uncapping process for caps of sample containers, the caps having different lengths, diameters, and types, and reusing uncapped caps.

Means for Solving the Problem

Aspects of the present invention provide the following arrangements to achieve the foregoing object.

Specifically, one arrangement includes: a first cap chuck that grips a cap; a second cap chuck disposed below the first cap chuck; and a third cap chuck disposed between the first cap chuck and the second cap chuck. The first cap chuck, the second cap chuck, and the third cap chuck each include at least three support bodies that grip the cap from a plurality of directions, and the third cap chuck includes the support bodies formed of an elastic material.

The cap is molded from, for example, rubber and plastic, functioning to prevent a sample stored in the sample container from leaking. The cap may be a screw cap screwed in place or a press-fitting cap press-fitted in place.

The sample container is a container in which a sample to be measured is sealed. The sample container may be mounted on a rack or a holder, as long as the sample container can be transferred.

The cap opening and closing mechanism may be any type as long as the type is controlled so as to be capable of performing an uncapping process that removes the cap and a capping process that mounts the cap. Preferably, the type is capable of holding and controlling the cap throughout entire processes from uncapping to capping. Nonlimiting examples of the cap opening and closing mechanism include one that uses a robot arm for the holding and the control, one that uses a turntable for the rotational holding and the control, and one that uses an elevator for the vertical holding and the control. The cap may be said to be held and controlled, if the cap and the container are properly prevented from being contaminated. Common approaches include shielding, suction and discarding, and cleaning and sterilization.

Another arrangement of the present invention is as follows.

Specifically, the another arrangement provides a sample processor having a transfer mechanism that transfers a sample container from which a cap can be removed and on which a cap can be mounted. The sample processor includes: storage means that stores therein uncapping and capping operations associated with each of different types of caps; determining means that determines at least either whether a cap compatible with the transferred sample container is mounted on the sample container or a type of the cap; and a cap opening and closing mechanism that performs uncapping and capping processes for the sample container. The cap opening and closing mechanism includes a first cap chuck; a second cap chuck disposed below the first cap chuck; a third cap chuck disposed between the first cap chuck and the third cap chuck, the third cap chuck being formed of an elastic material; at least three support bodies that grip the cap from a plurality of directions in each of the first cap chuck, the second cap chuck, and the third cap chuck; a clamp mechanism that controls a cap gripping operation performed by the support bodies; and an elevating mechanism that controls a vertical operation of the cap opening and closing mechanism. The sample processor includes a control unit that controls an operation of the cap opening and closing mechanism based on information on the type of the cap determined by the determining means and information relating to the uncapping and capping operations stored in the storage means.

The sample processor as used in the present invention refers to a system that includes a pre-processor that performs various types of pre-processes on the sample, including centrifugal separation, sub-sample pipetting, uncapping, capping, and affixing barcode labels. The system may include an automatic analyzer; however, the system needs only to include at least an uncapping mechanism, a capping mechanism, a pipetting mechanism, and a transfer mechanism that transfers samples among the foregoing mechanisms.

The sample container transfer mechanism may be any type as long as the type can transfer the racks and the holders. Common types of transfer mechanisms include ones incorporating a belt conveyor, a claw feed mechanism, or a robotic arm.

Effects of the Invention

In the aspect of the present invention, the sample container can be subjected to an uncapping process and a capping process using a single cap opening and closing mechanism included in the automatic analyzer. This offers an operator a wide choice of types of sample containers and achieves space saving and cost reduction in the automatic analyzer.

BRIEF DESCRIPTION OF THE DRAWINGS

FIG. 2B1 is an illustration showing an exemplary biological sample and an exemplary sample container to be loaded in the automatic analyzer.

FIG. 2B2 is an illustration showing an exemplary biological sample and an exemplary sample container to be loaded in the automatic analyzer.

FIG. 4B1 is an enlarged view showing an exemplary chuck mechanism.

FIG. 4B2 is an enlarged view showing an exemplary chuck mechanism.

MODES FOR CARRYING OUT THE INVENTION

The embodiment to be described below is an exemplary automatic analyzer including an opening and closing mechanism capable of performing with a single mechanism an uncapping process and a capping process for a sample container.

Figure 1:
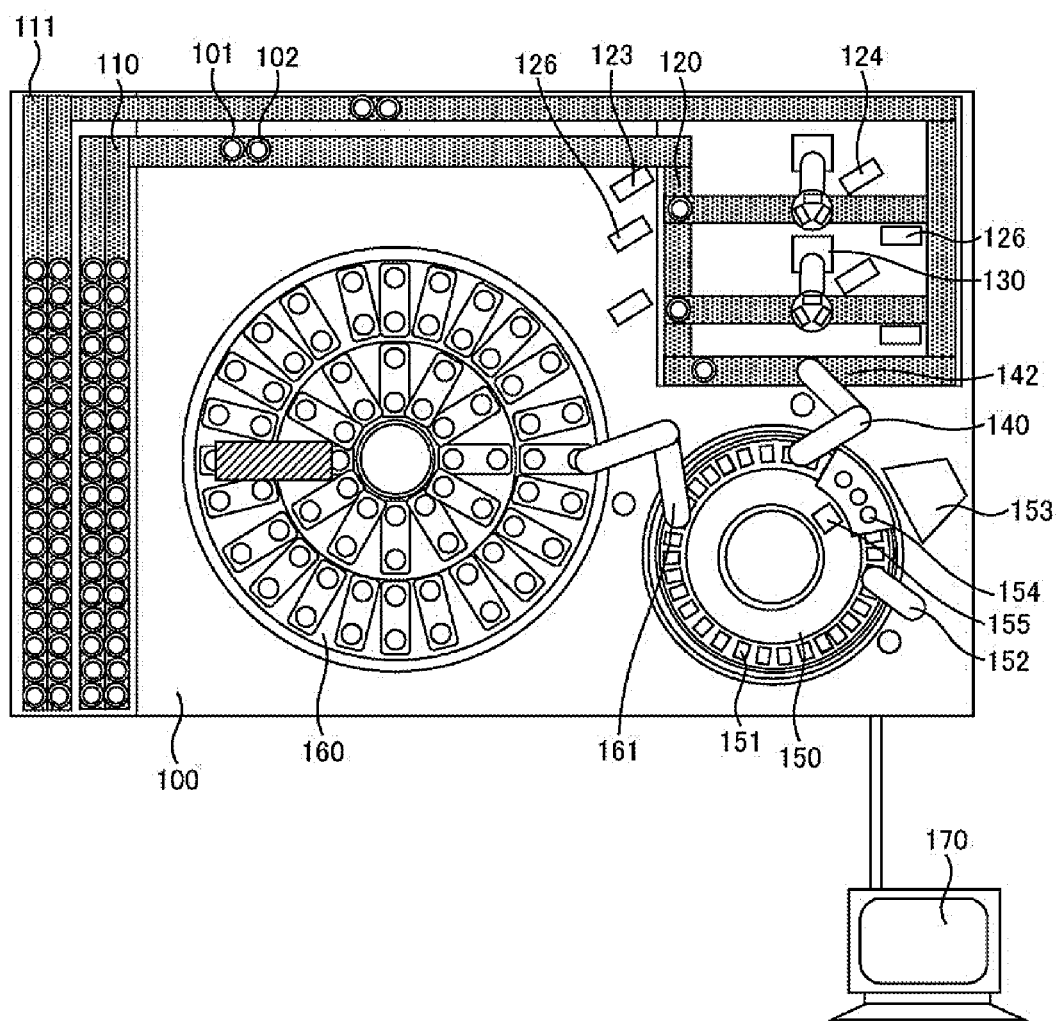
FIG. 1 is a configuration diagram showing an exemplary automatic analyzer according to an embodiment of the present invention.
Figure 2A:
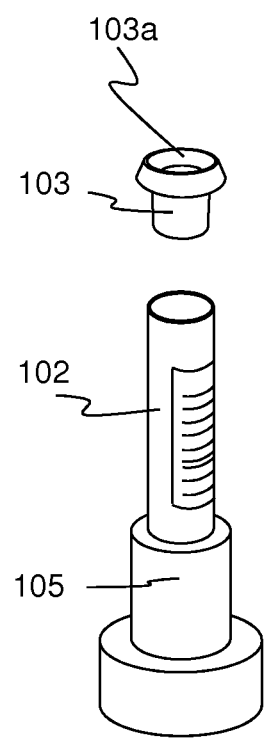
FIG. 2A is an illustration showing an exemplary biological sample and an exemplary sample container to be loaded in the automatic analyzer.
Figure 2C:
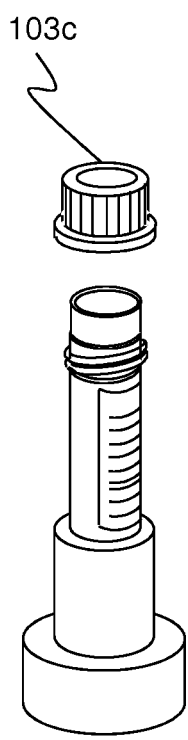
FIG. 2C is an illustration showing an exemplary biological sample and an exemplary sample container to be loaded in the automatic analyzer.
Figure 2D:
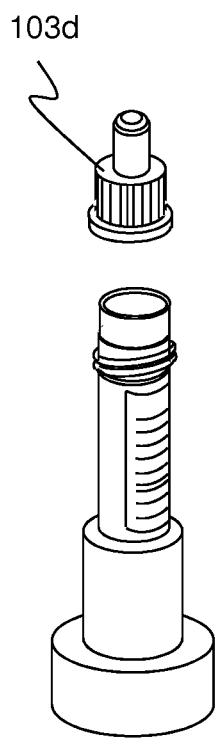
FIG. 2D is an illustration showing an exemplary biological sample and an exemplary sample container to be loaded in the automatic analyzer.
Figure 2E:
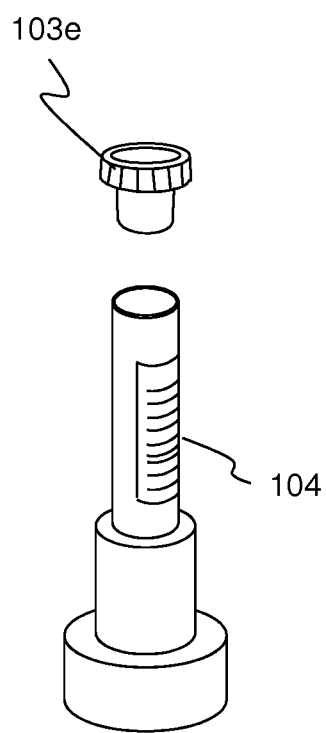
FIG. 2E is an illustration showing an exemplary biological sample and an exemplary sample container to be loaded in the automatic analyzer.

FIG. 1 is a configuration diagram showing an exemplary automatic analyzer according to the embodiment of the present invention.

This automatic analyzer 100 of the embodiment automatically analyzes components of a biological sample, such as blood and urine. The automatic analyzer 100 mainly includes a sample input buffer 110, a transfer mechanism 120, a cap opening and closing mechanism 130, a sample pipetting mechanism 140, a reaction disk 150, a reagent disk 160, and an automatic analyzer control computer 170. The automatic analyzer may have another configuration as long as such an automatic analyzer can achieve the configuration of the embodiment of the present invention. For example, the automatic analyzer may integrate a pre-processor with an analyzer.

A sample identification means 123 is disposed around the transfer mechanism 120 and reads a barcode 104 (see FIG. 4E) affixed to a sample container 102 being transferred, thereby obtaining information that identifies a sample 101 being transferred. The sample container 102 may be identified with a recording medium other than the barcode. For example, an arrangement may be made to include sample containers having RFID and the sample identification means 123 reads sample information (e.g., sample ID) stored in the recording medium. Additionally, the sample identification means may be an imaging device, such as a CCD.

In addition, cap detecting means 124 that can acquire information on whether a cap 103 is opened or closed and on the type of the cap 103 for the sample container being transferred may be installed as necessary. The cap detecting means 124 includes an imaging device, such as a CCD, images the sample container 102 to acquire an image thereof, analyzes the image, and determines an uncapped condition of the sample container 102 (whether the cap 103 is mounted) and the type of the cap 103. The cap detecting means 124 may use any method of cap detection other than that by image recognition to determine whether the cap is mounted and the type of the cap. For example, a light emitting element and a light receiving element may be disposed so as to face each other and an output of the light receiving element is detected to thereby determine whether the cap is mounted and the type of the cap. Still another method may be employed to detect whether the cap is mounted.

Preferably, the cap detecting means 124 is disposed, for example, near the cap opening and closing mechanism 130 as shown in FIG. 1. Prior to the uncapping and capping processes, the sample container 102 is imaged and the type of the cap is thereby determined. The cap opening and closing mechanism 130 is then instructed in optimum uncapping and capping methods. After the uncapping and capping processes are completed, a cap mounting condition of the sample container is checked again and it is determined whether the uncapping and capping processes have been properly performed. In the embodiment, the cap mounting condition before and after the uncapping and capping processes can be checked by the cap detecting means 124. In another embodiment including a plurality of cap opening and closing mechanisms 130, cap detecting means may be disposed at a position in a transfer path upstream of a corresponding cap opening and closing mechanism 130. This arrangement enables the sample container to be transferred to a specific cap opening and closing mechanism 130 that can most efficiently perform the uncapping and capping processes according to the type of the cap.

The cap opening and closing mechanism 130 has functions of removing the cap 103 from the sample container 102 transferred thereto, holding the removed cap 103, and mounting the removed cap 103 associated with the sample container 102.

The sample pipetting mechanism 140 uses a sample probe to pick up a biological sample through suction from the sample container 102 uncapped by the cap opening and closing mechanism 130 and discharge the biological sample into a predetermined reaction cell 151 on the reaction disk 150. The reaction disk 150 includes the reaction cell 151, a mixing device 152, a detecting device 153, and a cell washing mechanism 154. The reaction cell 151 mixes the biological sample with a reagent to cause reaction to take place therebetween. The mixing device 152 mixes a mixture in the reaction cell 151 to thereby promote reaction therebetween. The detecting device 153 measures an optical property of the mixture in the reaction cell 151 and transfers the acquired data to the control computer 170. The cell washing mechanism 154 cleans the reaction cell 151 that has undergone the measurement. The reagent disk 160 stores therein reagents required for component analysis of the biological sample. Additionally, a reagent probe 161 picks up through suction and discharges the reagent.

The control computer 170 controls each of the above-described operations and analyzes measured data. Understandably, the control computer is capable of communicating with each of the means and mechanisms described above and carrier identification means 126.

FIGS. 2A to 2E are illustrations showing exemplary biological samples and exemplary sample containers 102 to be loaded in the automatic analyzer 100.

The biological sample, after having been sampled, is sealed in a dedicated sample container 102. The sample container 102, before being loaded into the automatic analyzer 100, is fitted with a dedicated cap 103, so that entry of any extraneous substances can be prevented. Each cap 13 is fitted with a press-fitting cap (103*a*, 103*b*1, 103*b*2) (see FIGS. 2A, 2B1, and 2B2, respectively) or a screw cap (103*c*, 103*d*, 103*e*) (see FIGS. 2C, 2D, and 2E, respectively) that is suitable for the specific type of the sample container 102. The cap may be formed of an elastic body, such as rubber, or a hard material, such as a synthetic resin.

With a cap formed of a hard material, such as a synthetic resin, considerations need to be given to prevent an outer peripheral surface of the cap from being damaged or the cap body from being deformed as a result of an excessive load being applied to the cap during an automatic uncapping process. Additionally, depending on the type of the cap, the cap may be deeply inserted into the sample container. This restricts positions to be clamped of the cap during performance of the uncapping process and the capping process.

An information medium, such as the barcode 104, is affixed to the outer peripheral surface of the sample container 102. Instead of the barcode, for example, a two-dimension code or RFID may be affixed. The sample container 102 is placed on a dedicated carrier 105, such as a holder and a rack, and moved through the automatic analyzer 100.

Figure 3:
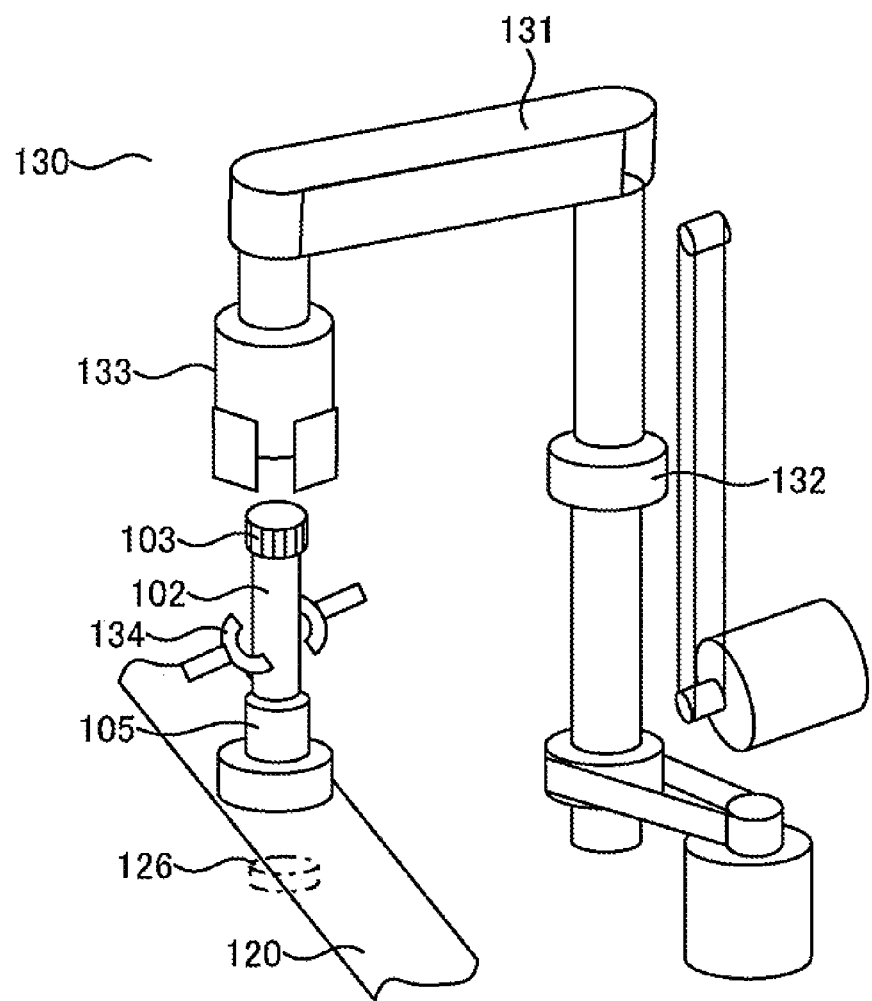
FIG. 3 is an illustration showing an exemplary cap opening and closing mechanism.

FIG. 3 is an illustration showing an exemplary cap opening and closing mechanism 130. The cap opening and closing mechanism 130 mainly includes an opening and closing arm mechanism 131, an opening and closing elevating mechanism 132, a clamp mechanism 134 for the sample container 102, and a chuck mechanism 133.

The opening and closing arm mechanism 131 moves the chuck mechanism 133. FIG. 3 shows that the chuck mechanism 133 is rotatably moved about a rotational shaft. This is, however, not the only possible arrangement. Alternatively, the opening and closing arm mechanism 131 may have an X-axis and a Y-axis and thereby move the cap chuck mechanism along an X-direction and a Y-direction.

The clamp mechanism 134 raises and fixes in place the sample container 102 during cap opening and closing operations.

The chuck mechanism 133 performs the uncapping and capping processes for the cap 103. The chuck mechanism 133 also holds the cap that has undergone the uncapping process for subsequent use in the capping process. Another possible arrangement may include a cap disposal site near the cap opening and closing mechanism 130, so that any removed cap that is no longer required can be discarded at the cap disposal site. Still another possible arrangement includes a site, disposed near the cap opening and closing mechanism 130, for supplying the cap 103. This arrangement can respond to a need for capping with a cap 103 dedicated to capping.

The carrier identification means 126 is disposed below the cap opening and closing mechanism 130. The carrier identification means 126 reads carrier ID information and sample ID information recorded on a recording medium of a carrier that carries the sample container 102 transferred to the cap opening and closing mechanism 130. The sample identifying information read by the sample identification means 123 and the carrier ID information read by the carrier identification means 126 are transmitted to the control computer 170. The control computer 170 associates the two pieces of information with each other to thereby create information that uniquely identifies the specific sample container 102 within the automatic analyzer 100.

Steps for the uncapping and capping processes for the sample container 102 and a sample pipetting process will be described below with reference to FIGS. 1 to 3.

When an operator loads the sample container 102 having therein a biological sample in the sample input buffer 110, the transfer mechanism 120 transfers the sample container 102 onto the automatic analyzer 100. Information on the sample container 102 transferred to the automatic analyzer 100 is transmitted to the control computer 170 via communication means within the automatic analyzer 100. With a response to this communication used as a trigger, the transfer mechanism 120 automatically transfers the sample container 102 to different mechanisms within the automatic analyzer 100.

The sample identification means 123 reads the barcode 104 and the carrier identification means 126 reads the implemented carrier ID information. The sample identification means 123 and the carrier identification means 126 then transmit data to the control computer 170. The control computer 170 associates the two pieces of information with each other to thereby create information that uniquely indicates the sample container 102 in question within the automatic analyzer 100.

The cap detecting means 124 includes an imaging device, such as a CCD, and analyzes the image of the sample container 102 to thereby determine the uncapped condition of the sample container 102 (whether the cap 103 is mounted) and the type of the cap 103. The cap detecting means 124 may use any method of cap detection other than that by image recognition to determine whether the cap is mounted and the type of the cap. For example, a light emitting element and a light receiving element may be disposed so as to face each other and an output of the light receiving element is detected to thereby determine whether the cap is mounted and the type of the cap. Still another method may be employed to detect whether the cap is mounted.

Based on the analyzed information, the control computer 170 determines specific details for processing the cap 103 (whether the uncapping process is required, the specific cap opening and closing mechanism 130 to be used, operating parameters of each of different mechanisms, and the like) and provides the transfer mechanism 120 with the information for use in its processing. For the carrier that carries a sample container for which the control computer 170 determines a necessity for an uncapping process, the cap opening and closing mechanism 130 performs the uncapping process for the cap 103. When the uncapping process is completed, the carrier identification means 126 disposed below the cap opening and closing mechanism 130 reads the carrier ID of the carrier that carries the sample container and transmits the information to the control computer 170. Thereby, the control computer 170 stores therein the carrier ID information and information on the "specific cap opening and closing mechanism 130 that has successfully completed the uncapping process". The foregoing steps allow the control computer 170 to associate information on each sample container 102 with the cap opening and closing mechanism 130 that has performed the uncapping process.

The cap opening and closing mechanism 130 also has a function of storing the removed cap 103 until the capping process to be described later is performed. When a removed cap is to be held, no new sample container 102 is to be subjected to an uncapping process. If the capping process is not required, the cap that has undergone the uncapping process is moved to, and discarded at, the cap disposal site. If the capping process is performed using a new cap 103 dedicated to capping, the cap that has undergone the uncapping process is discarded at the cap disposal site and the new cap 103 is picked up from a supply site 135 adjacent thereto for use in the capping process.

The sample container 102 that has undergone the uncapping process is transferred onto a sample pipetting position 142 and subjected to a sample pipetting process in order of arrival at the sample pipetting position 142. A carrier identification means 126 is also disposed below the sample pipetting position 142. The carrier identification means 126 reads the carrier ID information and transmits the same to the control computer 170. The control computer 170 stores therein the carrier ID information associated with information that the "pipetting process has been successful".

The sample container 102 that has undergone the pipetting process, if requiring a capping process, is transferred onto the cap opening and closing mechanism 130 again. As the sample container 102 reaches an area in which the carrier identification means 126 can identify the carrier ID, the carrier identification means 126 reads the carrier ID information and transmits the same to the control computer 170.

The control computer 170 collates the carrier ID information transmitted thereto with the carrier ID information transmitted thereto during the uncapping process to thereby identify the cap opening and closing mechanism 130 that has performed the uncapping process for the sample container 102 in question. Based on the collated information, the control computer 170 determines a necessity for the capping process and transfers the sample container to an appropriate cap opening and closing mechanism 130. The necessity for the capping process is determined based on information including that on a specific process appropriate for the sample container 102, such as, for example, whether the capping process is required, the type of the cap opening and closing mechanism 130 to be used, and operating parameters of different mechanisms of the cap opening and closing mechanism 130 (e.g., the position at which the chuck mechanism 133 grips the cap, a normal torque range during the capping process).

The capping process is performed when the sample container 102 is transferred so as to be returned to the cap opening and closing mechanism 130 again as described above. The foregoing steps allow the cap 103 that has originally been mounted on the sample container 102 before the uncapping process to be mounted back again on the sample container 102 that has undergone the pipetting process. After the capping process, the carrier identification means 126 transmits the read carrier ID information to the control computer 170 and the control computer 170 stores therein information that the "capping process has been successful" together with the carrier ID.

The sample container 102 that has undergone the capping process is transferred onto a sample buffer 111 along the path of the transfer mechanism 120. The sample container 102 is stored in a position specified by the control computer 170.

Figure 4A:
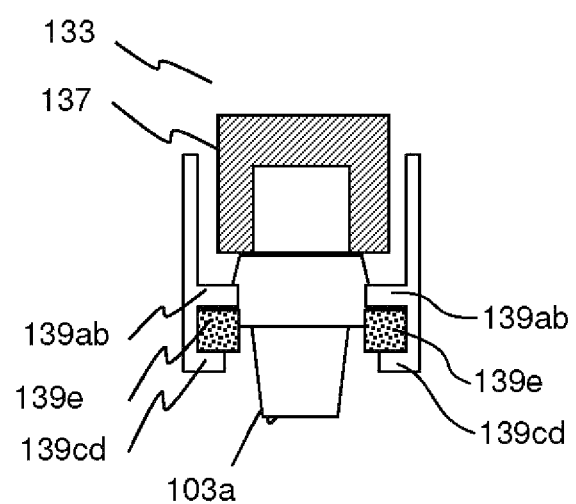
FIG. 4A is an enlarged view showing an exemplary chuck mechanism.
Figure 4C:
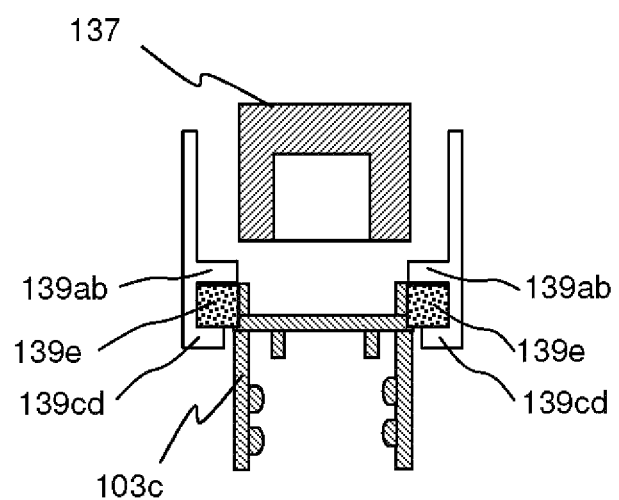
FIG. 4C is an enlarged view showing an exemplary chuck mechanism.
Figure 4D:
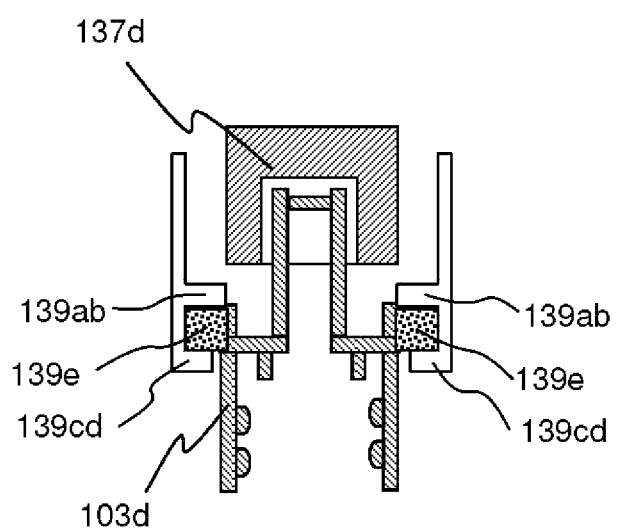
FIG. 4D is an enlarged view showing an exemplary chuck mechanism.
Figure 4E:
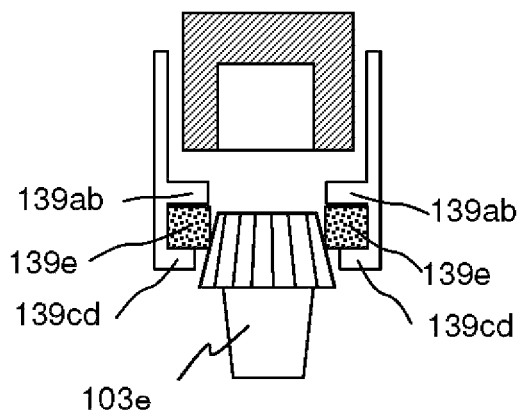
FIG. 4E is an enlarged view showing an exemplary chuck mechanism.
Figure 4F:
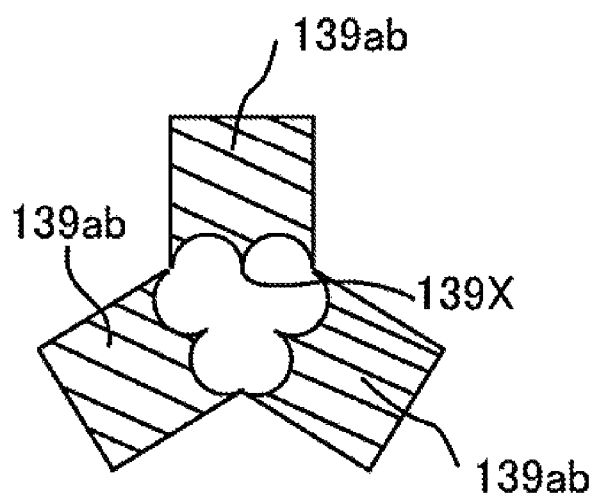
FIG. 4F is an enlarged cross-sectional view showing an exemplary chuck mechanism.
Figure 4G:
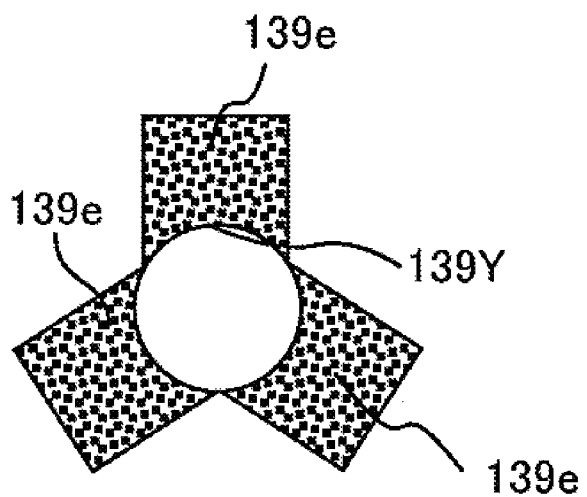
FIG. 4G is an enlarged cross-sectional view showing an exemplary chuck mechanism.
Figure 4H:
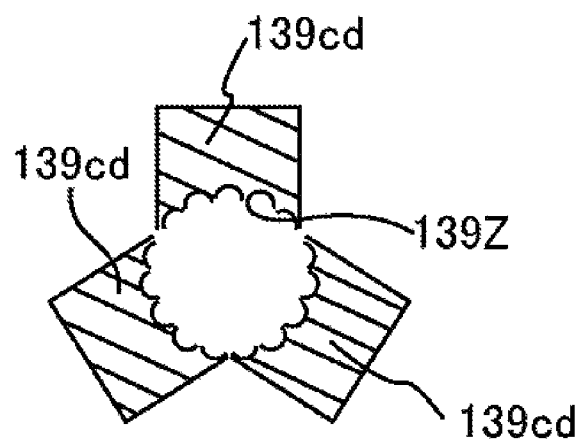
FIG. 4H is an enlarged cross-sectional view showing an exemplary chuck mechanism.

FIGS. 4F, 4G, and 4H are enlarged cross-sectional views showing exemplarily how the chuck mechanism 133 grips each of different types of cap. The cap opening and closing mechanism 130 as a characteristic aspect of the present application will be described below with reference to FIGS. 4A to 4H.

The chuck mechanism 133 includes a cap chuck set 139 for gripping the cap 103. The cap chuck set 139 in the embodiment of the present invention includes a cap chuck 139ab having a shape suitable for uncapping and capping processes of the press-fitting caps (103a, 103b1, 103b2) and a cap chuck 139cd having a shape suitable for uncapping and capping processes of the screw caps (103c, 103d, 103e). The cap chuck 139ab and the cap chuck 139cd are spaced apart from, and overlap, each other in a vertical direction. Preferably, a cap chuck 139e formed of an elastic material is disposed to be sandwiched between the cap chuck 139ab and the cap chuck 139cd.

Each of the cap chucks includes a plurality of support bodies and has a space at a center thereof for gripping and holding the cap during the uncapping and capping processes. Preferably, the support bodies comprise three or more support bodies in order to prevent the cap from being damaged or deformed during the uncapping process due to load being concentrated on portions at which the support bodies and the cap contact each other.

In addition, a space defined by the plurality of support bodies of the cap chuck 139ab is smaller than a space defined by the plurality of support bodies of the cap chuck 139cd. A space defined by the plurality of support bodies of the cap chuck 139e is even smaller than the space defined by the plurality of support bodies of the cap chuck 139ab.

The cap chucks (139ab, 139cd) are each formed of, for example, stainless steel or other metal and the cap chuck 139e is formed of, for example, rubber. Additionally, the cap chuck 139ab and the cap chuck 139cd have a plurality of protrusions 139X and a plurality of protrusions 139Z, respectively, the protrusions protruding to contact the cap 103 (see FIGS. 4F and 4H).

A process for gripping the press-fitting caps (103a, 103b1, 103b2) will first be described below with reference to FIGS. 4A and 4B1, 4B2. FIGS. 4A and 4B1, 4B2 are illustrations showing the chuck mechanism 133 in the embodiment of the present invention gripping different types of press-fitting caps.

The cap chuck 139ab for the press-fitting caps (103a, 103b1, 103b2) is spaced upwardly apart from the cap chuck 139cd for the screw caps (103c, 103d, 103e). The protrusions 139X of the cap chuck 139ab to be in contact with the press-fitting cap protrude more relative to the cap than the protrusions 139Z of the cap chuck 139cd to be in contact with the screw cap do. When the chuck mechanism 133 grips the cap 103 in the space in the cap chuck, therefore, the protrusions 139X of the cap chuck 139ab first press the cap 103 and, when the cap 103 is deformed to be depressed, the cap chuck 139e of the elastic material presses to hold the cap 103.

The foregoing steps cause the protrusions 139X to press the cap when the cap chuck 139ab grips the cap 103, so that a chucking force can be easily transmitted, thus enabling the cap 103 to be gripped without slipping. Further press-fitting causes the cap chuck 139e or the cap chuck 139cd having a greater number of protrusions (preferably having a circular shape) to press the cap 103. This prevents uneven load to be applied in a circumferential direction to the cap 103 through the uncapping process, so that the cap 103 can be prevented from being deformed or damaged.

During capping, similarly, the protrusions 139X of the cap chuck 139ab fix the cap 103 in place and the cap chuck 139cd and the cap chuck 139e transmit the force of the chuck mechanism to the cap 103; moreover, a support section 137 disposed at an upper portion of each of these cap chucks exerts a downward force on the cap 103 from above, so that the capping process can be performed with the cap being press-fitted from above.

A process for gripping the screw caps (103c, 103d, 103e) will next be described below with reference to FIGS. 4C, 4D, and 4E. FIGS. 4C, 4D, and 4E are illustrations showing the chuck mechanism 133 in the embodiment of the present invention gripping different types of screw caps.

The screw cap is a type of cap that can be screwed in a particular direction to be opened or closed. Generally, the screw cap has a plurality of grooves formed in an outer peripheral surface thereof for preventing slippage during screwing.

The cap chuck 139cd for the screw caps (103c, 103d, 103e) is disposed below the cap chuck 139e formed of the elastic material. The protrusions 139Z of the cap chuck 139cd are disposed at positions recessed relative to the cap from a contact line (139Y, see FIG. 4G) of the cap chuck 139e formed of the elastic material. Thus, when the chuck mechanism 133 is to grip the screw cap 103, the elastic cap chuck 139e first presses the cap 103 and, when the cap chuck 139e is then deformed and depressed, the protrusions 139Z of the cap chuck 139cd having a greater number of protrusions press the cap 103.

If the cap chuck 139ab having the protrusions 139X protruding more relative to the cap than the cap chuck 139cd contacts the cap, the protrusions 139X can damage the cap. To prevent this from occurring, the control computer 170 directs a descent amount of the opening and closing elevating mechanism 132 so that the chuck mechanism 133 is positioned at a height at which the cap chuck 139ab does not contact the cap.

In addition, the support section 137 disposed at the upper portion of the cap chuck has an opening 137d that avoids interference with a cylindrical protrusion disposed at an upper portion of the cap 103d, so that the cap can be reliably gripped in position.

The foregoing arrangements allow the elastic material of the cap chuck 139e and the protrusions 139Z of the cap chuck 139cd, both protruding relative to the cap, to fit into the grooves in the outer peripheral surface of the screw type cap 103. This enables the uncapping and capping processes to be performed on the cap reliably without involving slippage.

In addition, the cap chuck 139cd and the cap chuck 139e each have three or more support bodies, which allows the cap 103 to be gripped in a straight position. This prevents failure in the uncapping and capping processes due to a tilted cap 103. At the same time, the cap chuck 139e is formed of an elastic material and has the protrusions that together form a circular shape. This achieves a greater contact area relative to the cap 103 to thereby allow the chucking force to be transmitted efficiently. Additionally, as described earlier, when the cap chuck 139e or the cap chuck 139cd having a greater number of protrusions (preferably having a circular shape) grips the cap 103, a chucking force relative to the cap 103 can be prevented from being unevenly applied in a circumferential direction of the cap, so that the cap 103 can be prevented from being deformed.

In another possible arrangement, the cap chuck 139ab, the cap chuck 139cd, and the cap chuck 139e may be combined to achieve a positional relation thereamong variable relative to a direction in which the cap 103 is clamped. Specifically, each of the cap chucks is controlled to be open a variable amount and, immediately after the start of the uncapping or capping operation, the cap is lightly gripped to thereby be prevented from being deformed or damaged; at the end of the uncapping or capping operation, the cap is gripped firmly, to thereby enable the cap to be reliably removed or mounted. This permits flexible response to different outside diameters, different types of material, and different levels of hardness of the cap 103. The uncapping and capping processes can thus be performed without fail for any type of cap 103.

As described above, the chuck mechanism 133 according to the embodiment of the present invention combines the cap chuck 139ab and the cap chuck 139cd having shapes suitable for the respective shapes of the cap, with the cap chuck 139e. The cap 103, whether it be a press-fitting cap or a screw cap, can therefore be prevented from being deformed or damaged, or from slipping. The chuck mechanism 133 thus enables gripping required for uncapping and capping, avoiding failure in the uncapping or capping process for the cap 103.

Figure 5:
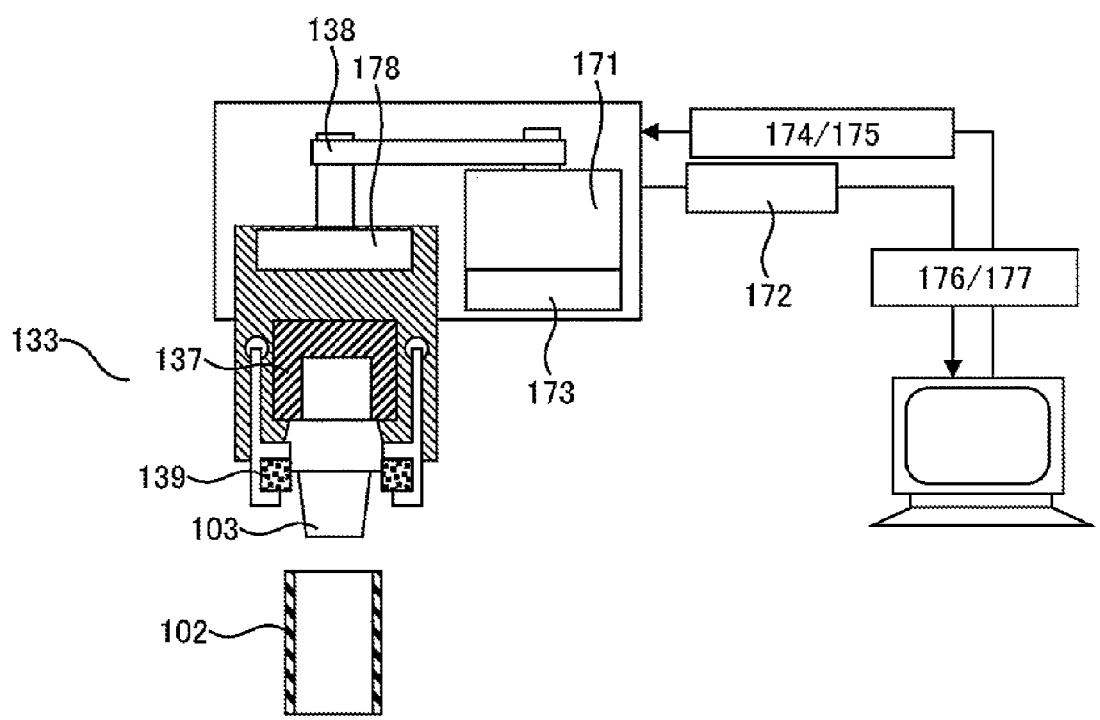
FIG. 5 is an illustration showing an exemplary chuck rotating mechanism.

FIG. 5 is a schematic illustration showing an exemplary chuck rotating mechanism 138.

The chuck mechanism 133 includes mainly the support section 137, the cap chuck set 139, the chuck rotating mechanism 138, a force sensor 178, and an encoder 173. Specifically, the support section 137 contacts an upper end surface of the cap 103. The cap chuck set 139 grips the outer peripheral surface of the cap 103. The chuck rotating mechanism 138 rotates the cap 103 gripped in place. The force sensor 178 detects torque applied to the cap chuck mechanism.

The chuck rotating mechanism 138 is rotatable both in an uncapping direction and a capping direction by a motor 171. With the opening and closing elevating mechanism 132 not shown in figure, the chuck rotating mechanism 138 is capable of making an upward motion in the uncapping direction and a downward motion in the capping direction.

The motor 171 and an elevating motor not shown in figure are driven through control by the control computer 170.

An ammeter 172 detects drive current of the motor 171 and applies the drive current to the control computer 170. The control computer 170 can then calculate torque using the current value.

The encoder 173 is disposed at the motor 171 and counts pulses output through rotation of the motor 171, so that the control computer 170 can calculate an angle of rotation of the chuck mechanism 133.

Meanwhile, the control computer 170 outputs a command signal for controlling drive of the motor 171. The control computer 170 can output a torque command signal 174 that controls tightening torque of the cap 103 achieved through the rotation of the chuck mechanism 133 and angle of rotation and speed command signals 175 of the cap 103.

Exemplary uncapping and capping processes for the cap 103 performed by the chuck mechanism 133 will be described below with reference to FIGS. 3 to 5.

As described earlier, when the uncapped condition of the sample container 102 and the type of the cap 103 are identified, the control computer 170 determines details of the uncapping and capping processes for the sample container 102 based on the analyzed information. The details of the uncapping and capping processes may have been registered by the operator in advance.

If the type of the cap 103 of the sample container 102 is the press-fitting cap (103a, 103b1, 103b2), the opening and closing elevating mechanism 132 and the chuck rotating mechanism 138 are made to be operative by a command from the control computer 170 and the uncapping process is performed to rotate and raise the cap 103 for uncapping and the capping process is performed to rotate and push into position the cap 103 for capping.

For the screw cap (103c, 103d, 103e), while rotating operations involving, for example, torque and speed values different from those with the press-fitting cap (103a, 103b1, 103b2) are performed, an ascent operation and a descent operation are performed according to a screw pitch in accordance with an instruction from the control computer 170. As such, according to the information on the sample container 102 and the cap 103, operating parameters, such as torque and speed, are changed as necessary during the uncapping and capping operations to thereby enable optimum uncapping and capping processes to be achieved.

The capping process for the press-fitting cap (103a, 103b1, 103b2) generally requires a large pressure and a high rotational torque. In contrast, the capping process for the screw cap (103c, 103d, 103e) requires a small pressure and a low rotational torque. As described earlier, a specific cap chuck selected according to the information on the sample container 102 and the cap 103 is used in the cap chuck set 139 that grips the cap 103 (the cap chuck 139ab for the press-fitting cap or the cap chuck 139cd for the screw cap). As a result, the cap chuck set 139 can transmit the rotational torque applied by the chuck rotating mechanism 138 to the cap 103 as a tightening torque requirement. In either case, the cap 103 can be prevented from slipping during rotation.

The present invention is characterized by comprising the cap chuck set 139 that simultaneously satisfies the foregoing contradictory requirements for the shape of the cap chuck set 139.

Figure 6:
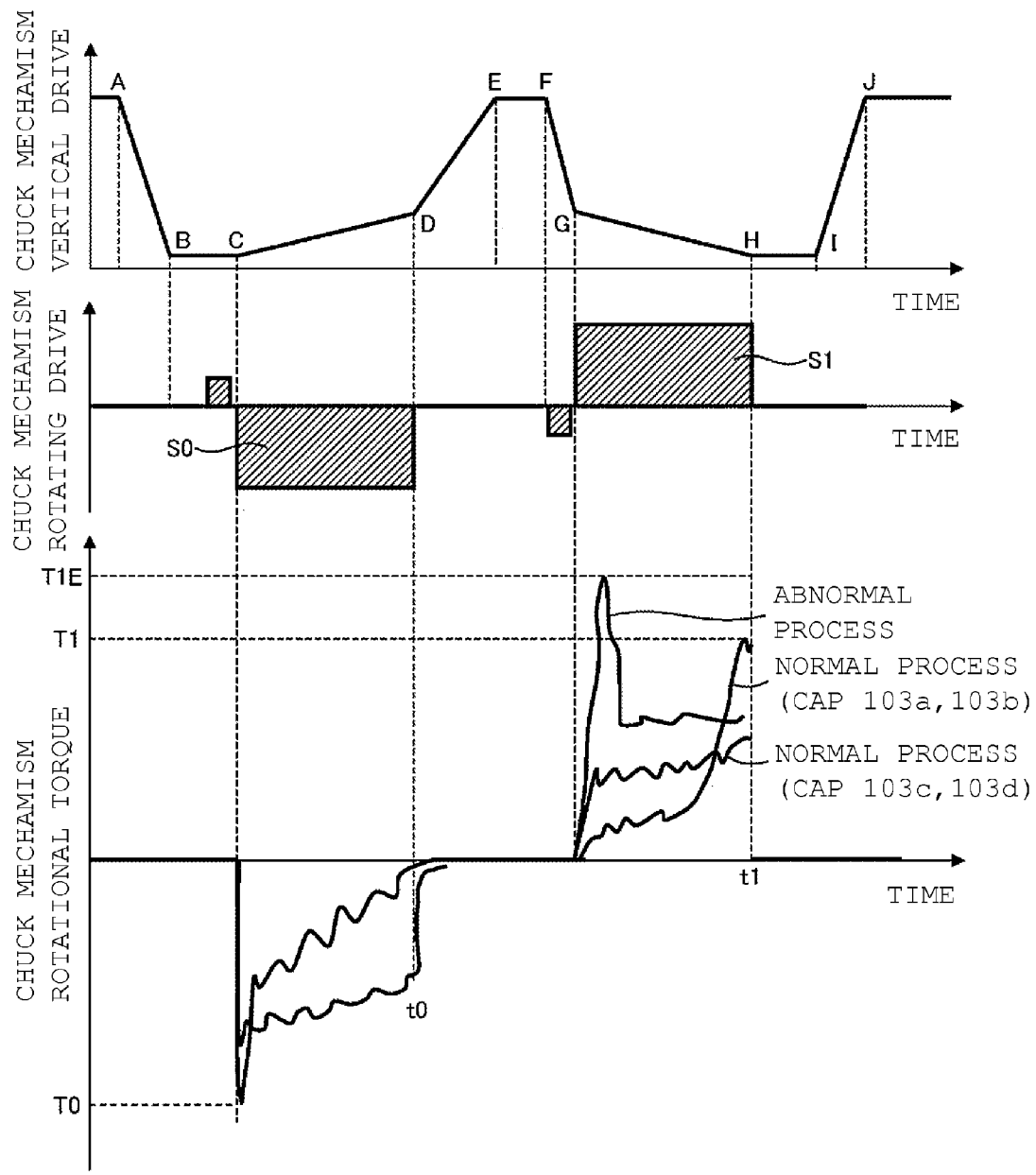
FIG. 6 is an exemplary timing chart of the chuck mechanism.

FIG. 6 is an exemplary timing chart for the uncapping and capping processes, with attention focused on the vertical motion of the chuck mechanism 133 and the rotational motion and rotational torque of the chuck rotating mechanism 138 in the cap opening and closing mechanism 130.

The upper chart of FIG. 6 shows a driving height of the chuck mechanism 133 achieved by the opening and closing elevating mechanism 132. The middle chart of FIG. 6 shows the rotational speed of the chuck rotating mechanism 138 achieved by the motor 171. The lower chart of FIG. 6 shows the tightening torque of the chuck rotating mechanism 138.

Exemplary uncapping and capping processes for the cap 103 performed by the chuck mechanism 133 will be described below with reference to FIGS. 3 to 6.

As described earlier, the sample container 102 is transferred by the transfer mechanism 120 and stopped at an uncapping/capping position in the cap opening and closing mechanism 130. This stage corresponds to a step in the upper chart of the timing chart of FIG. 6 before "A".

(Steps for A to C) The chuck mechanism 133 is lowered by the opening and closing elevating mechanism 132 (section A-B in the upper chart of FIG. 6) and grips the cap 103 at position C. Positioning of the chuck rotating mechanism 138 may be performed at this time. In the middle chart of FIG. 6, the chuck rotating mechanism 138 rotates in section B-C and performs a zero return operation.

(Steps for C to D) With the cap 103 gripped by the chuck mechanism 133, the chuck rotating mechanism 138 rotates as the opening and closing elevating mechanism 132 operates. At this time, the torque command signal 174 and the angle of rotation and speed command signals 175 are transmitted from the control computer 170 to the motor 171. The chuck rotating mechanism 138 that grips the cap 103 controls the resultant rotation by this drive of the motor 171.

Through the drive of the motor 171, the chuck mechanism 133 starts rotating from position C of the upper chart of FIG.

6 and stops rotating as a command angle of rotation S0 is reached at position D. A maximum rotational torque at this time is T0 representing a value that is so sufficiently high that an actual speed follows the command speed. In section C-D, the chuck mechanism 133 is rotated in the uncapping direction and raised and, at a point in time D, the uncapping process is completed.

(Steps for D to E) When the uncapping process is completed, the chuck mechanism 133 raises to pull the cap 103 upwardly from an opening in the sample container 102. The chuck mechanism 133 starts rising from position D in the upper chart of FIG. 6 and, when the chuck mechanism 133 reaches position E, the cap 103 can be completely removed from the opening in the sample container 102.

(Steps for E to F) The chuck mechanism 133 holds the cap 103. The chuck mechanism 133 stays at this height (section E-F of the upper chart of FIG. 6) until the sample that has undergone the uncapping process undergoes the sample pipetting process and returns to the position of the cap opening and closing mechanism 130.

Then, the transfer mechanism 120 transfers the sample container 102 that has undergone the sample pipetting process and brings the sample container 102 to a stop at the uncapping/capping position of the cap opening and closing mechanism 130.

(Steps for F to G) The chuck mechanism 133 holding the cap 103 in place is lowered by the opening and closing elevating mechanism 132. Positioning of the chuck rotating mechanism 138 may be performed at this time.

(Steps for G to H) Concurrently with the descent motion by the opening and closing elevating mechanism 132 for the chuck mechanism 133 that holds the cap 103 therein, the chuck rotating mechanism 138 is rotated. The rotating operation of the chuck rotating mechanism 138 involves the torque command signal 174 and the angle of rotation and speed command signals 175 being transmitted from the control computer 170 to the motor 171 and the resultant drive of the motor 171 rotating the chuck mechanism 133 that holds the cap 103 therein.

Through the drive of the motor 171, the chuck mechanism 133 starts rotating from a point in time G of the upper chart of FIG. 6 and stops rotating as a command angle of rotation S1 is reached at a point in time H. Meanwhile, the maximum value of command torque is T1 representing a value that is so sufficiently high that the actual speed follows the command speed (the chuck mechanism 133 is rotated in the capping direction; the chuck mechanism 133 lowers in section G-H and the capping process is completed at a point in time H).

(Steps for H to I) It is determined whether the capping process has been normally completed. The lower chart of FIG. 6 shows an exemplary rotational torque in an abnormally completed process. As described earlier, a fault that may occur during a capping or uncapping process for the cap 103 can be detected by detecting using the force sensor 178 torque during the capping process for the cap 103. For example, a normal torque value range is set in advance and a fault may be determined to have occurred in the uncapping or capping process when torque falls outside the range. Alternatively, torque waveform patterns during the normal uncapping and capping processes are stored in memory and a fault may be determined to have occurred when a torque waveform actually measured with the force sensor 178 differs from the normal torque waveform patterns. Additionally, although the embodiment has been described for a determination made for the capping process, a determination for an uncapping process may be made similarly for section E-F.

(Steps for I to J) When the capping process is completed, the chuck mechanism 133 rises and waits for a subsequent process.

The foregoing processes enable a capping fault to be monitored through, for example, detection of torque or load. Capping faults include, for example, a case in which the chuck mechanism 133 grips a cap 103 in a tilted position and the cap 103 is obliquely pressed into the sample container 102, resulting in an incomplete capping condition.

The operator may be informed of an incomplete uncapping or capping process that may be detected. For example, if the control computer 170 has a display, the display may give a corresponding alarm message. Alternatively, an alarm or indicator lamp may be turned on to raise caution. In this case, the operator visually checks the condition of the sample and, if a cause of the fault is noted, performs a recovery procedure to eliminate the cause. If an incompletely capped condition is noted, the operator may opt for a retry operation (any faultily capped cap is uncapped and recapped) to achieve a complete capping process. These steps bring the operation to a normal one.

Effects of the embodiment described heretofore will be described below.

To perform the uncapping and capping processes and the sample pipetting process for sample containers in a sample line of an automatic analyzer, the related-art arrangements typically include an uncapping mechanism and a capping mechanism disposed separately from each other, the uncapping mechanism and the capping mechanism being compatible with a specific type of cap. To enable a single mechanism to perform both the uncapping and capping processes, the mechanism tends to be complicated in order to satisfy the need to respond to caps having different shapes and uncapping and capping operations designed for different types of caps, such as the press-fitting type and the screw type. Thus, a dedicated cap is used for the capping process and it has been considered difficult to re-use in the capping process the cap that has been applied to hermetically seal the sample container. Additionally, the capping process using the dedicated cap typically works on the press-fitting style in sealing the sample container. It has thus been difficult to determine accurately a capping fault.

To achieve the foregoing object, the embodiment of the present invention includes, in order to re-use a cap removed from a sample container through an uncapping process for capping the same sample container, a control system that associates the cap with the sample container and a cap chuck set that holds and controls the cap that has undergone an uncapping process, thereby enabling the sample container requiring capping to be capped with the original cap. This allows the caps to be re-used reliably.

The embodiment further includes a plurality of cap chucks adaptable to different materials used for the cap and uncapping and capping styles and a control unit that changes the angle of rotation and the uncapping and capping operations including the vertical drive according to the type of the cap being worked on. Thus, a single uncapping and capping mechanism can perform uncapping and capping processes for a plurality of types of caps.

The embodiment of the present invention can thus provide an automatic analyzer including a cap opening and closing mechanism capable of reliably performing uncapping and capping processes for sample containers.

DESCRIPTION OF REFERENCE NUMERALS

100: Automatic analyzer
102: Sample container
103: Cap
104: Barcode
105: Carrier
110: Sample input buffer
111: Sample buffer
120: Transfer mechanism
123: Sample identification means
124: Cap detecting means
126: Carrier identification means
130: Cap opening and closing mechanism
131: Opening and closing arm mechanism
132: Opening and closing elevating mechanism
133: Chuck mechanism
134: Clamp mechanism
137: Support section
138: Chuck rotating mechanism
139: Cap chuck set
140: Sample pipetting mechanism
142: Sample pipetting position
150: Reaction disk
151: Reaction cell
152: Mixing device
153: Detecting device
154: Cell washing mechanism
155: Light source
160: Reagent disk
170: Control computer
171: Motor
172: Ammeter
173: Encoder
174: Torque command signal
175: Speed command signal
176: Database
177: Determining means

The invention claimed is:

1. A cap opening and closing mechanism comprising:
a first cap chuck that grips a cap, and that includes at least three support bodies that grip the cap from a plurality of directions;
a second cap chuck disposed below the first cap chuck, and that includes at least three support bodies that grip the cap from the plurality of directions; and
a third cap chuck disposed between the first cap chuck and the second cap chuck in the vertical direction, and that includes at least three support bodies that grip the cap from the plurality of directions,
wherein the support bodies of the third cap chuck are formed of an elastic material.

2. The cap opening and closing mechanism according to claim 1, wherein
the support bodies of the first cap chuck and the support bodies of the second cap chuck each have one or more protrusions, and
the protrusions of the support bodies of the first cap chuck differ in shape from the protrusions of the support bodies of the second cap chuck.

3. The cap opening and closing mechanism according to claim 2, wherein the protrusions of the support bodies of the first cap chuck protrudes more relative to the cap than the protrusions of the support bodies of the second cap chuck.

4. The cap opening and closing mechanism according to claim 1, wherein the support bodies of the third cap chuck protrude more relative to the cap than the support bodies of the first cap chuck and the second cap chuck.

5. An automatic analyzer having a transfer mechanism that transfers a sample container from which a cap can be removed and on which a cap can be mounted, the automatic analyzer comprising:
a cap opening and closing mechanism, the cap opening and closing mechanism including:
a first cap chuck, and that includes at least three support bodies that grip the cap from a plurality of directions;
a second cap chuck disposed below the first cap chuck, and that includes at least three support bodies that grip the cap from a plurality of directions;
a third cap chuck disposed between the first cap chuck and the second cap chuck in a vertical direction, and that includes at least three support bodies that the cap from a plurality of directions; and
a clamp that grips the sample container.

6. The automatic analyzer according to claim 5, further comprising:
an imaging device configured to capture an image of the sample container,
wherein the opening and closing mechanism is mounted on an arm connected to a drive assembly that is configured to raise or lower the opening and closing mechanism in the vertical direction,
wherein the automatic analyzer further comprises a computer that is connected to each of the imaging device and the drive assembly, and
wherein the computer is programmed to determine a type of the cap of the sample container based on the image of the sample container captured by the imaging device and control an operation of the cap opening and closing mechanism based on the type of the cap.

7. The automatic analyzer according to claim 6, wherein the computer is programmed to control at least one of a position at which each of the support bodies in the cap opening and closing mechanism grips the cap, an angle of rotation of the cap, and a displacement amount of an elevating mechanism involved in uncapping and capping processes.

8. The automatic analyzer according to claim 6, further comprising:
an information reader reading identification information of a sample disposed near the transfer mechanism that transfers the sample container to be subject to an uncapping process performed by the cap opening and closing mechanism; and
a storage device storing therein the sample identification information read by the information reader,
wherein the computer stores the identification information of the sample in association with information of the cap opening and closing mechanism in which the uncapping process is performed.

9. The automatic analyzer according to claim 8, further comprising:
wherein the computer is programmed to identify the cap opening and closing mechanism that has performed the uncapping process for the cap of the sample container based on the identification information identified by the information reader and control the transfer mechanism to transfer the sample container to be subject to the capping process to the cap opening and closing mechanism.

10. The automatic analyzer according to claim 5, wherein the cap opening and closing mechanism holds the cap removed by the uncapping process until the capping process is performed.

11. The automatic analyzer according to claim 6, further comprising:

a rotating mechanism, including a motor, that is connected to each of the first cap chuck, second cap chuck, and third cap chuck, wherein the computer is connected to the rotating mechanism, and wherein the computer is programmed to control the rotating mechanism to rotate at least one of the first cap chuck, second cap chuck, and third cap chuck and simultaneously control the drive assembly to raise the opening and closing mechanism in the vertical direction.

12. The automatic analyzer according to claim 11, further comprising:

a sensor that detects load applied at least either the rotating mechanism or the elevating mechanism, wherein the computer is programmed to determine that a fault occurs in the uncapping or capping process when the load detected by the sensor falls outside a predetermined range.

13. The automatic analyzer according to claim 12, wherein the computer is programmed to output a notification of a fault when the computer detects the fault in the uncapping or capping process.

14. The automatic analyzer according to claim 12, wherein the computer is further programmed to perform a retry operation of an uncapping or capping process, if the control unit has detected a fault in the uncapping or capping process.

15. The automatic analyzer according to claim 8, wherein the information reader is one of a barcode reader, a radio-frequency identification (RFID) reader, and an image capture device.

* * * * *